(12) United States Patent
Cetin

(10) Patent No.: US 12,286,613 B2
(45) Date of Patent: Apr. 29, 2025

(54) PORTABLE INCUBATOR PLATFORM INTEGRATED INTO A PORTABLE IMAGING DEVICE

(71) Applicant: IZMIR BIYOTIP VE GENOM MERKEZI, İzmir (TR)

(72) Inventor: Arif Engin Cetin, Izmir (TR)

(73) Assignee: IZMIR BIYOTIP VE GENOM MERKEZI, Izmir (TR)

( * ) Notice: Subject to any disclaimer, the term of this patent is extended or adjusted under 35 U.S.C. 154(b) by 708 days.

(21) Appl. No.: 17/639,916

(22) PCT Filed: Aug. 31, 2020

(86) PCT No.: PCT/TR2020/050786
§ 371 (c)(1),
(2) Date: Mar. 3, 2022

(87) PCT Pub. No.: WO2021/050023
PCT Pub. Date: Mar. 18, 2021

(65) Prior Publication Data
US 2022/0340857 A1    Oct. 27, 2022

(30) Foreign Application Priority Data
Sep. 10, 2019    (TR) .............................. TR2019/13661

(51) Int. Cl.
*C12M 1/00*    (2006.01)
*C12M 1/34*    (2006.01)
(Continued)

(52) U.S. Cl.
CPC ............ *C12M 41/14* (2013.01); *C12M 23/54* (2013.01); *C12M 41/34* (2013.01); *C12M 41/36* (2013.01);
(Continued)

(58) Field of Classification Search
CPC ...... C12M 23/54; C12M 41/14; C12M 41/34; C12M 41/36; C12M 41/48; G01N 2015/1006; G01N 2015/144; G01N 2021/158; G01N 2021/6419; G01N 2021/6421; G01N 2021/6482;
(Continued)

(56) References Cited

U.S. PATENT DOCUMENTS 9,643,184 B2    5/2017    Zheng et al.
2016/0004057 A1    1/2016    Lin et al.
2017/0248592 A1    8/2017    Wang et al.

FOREIGN PATENT DOCUMENTS

JP    4626768 B2    2/2011

OTHER PUBLICATIONS

Maria P. Walzik, et al., A portable low-cost long-term live-cell imaging platform for biomedical research and education, Biosensors and Bioelectronics, 2015, pp. 639-649, vol. 64.
(Continued)

*Primary Examiner* — Lydia Edwards
(74) *Attorney, Agent, or Firm* — Bayramoglu Law Offices LLC

(57) ABSTRACT

A portable incubator system integrated to a mobile phone providing a real-time tracking of samples and data flow is provided. The portable incubator system allowing cells to be cultured, reproduced and characterized in real-time without a need for a commercial incubator and a microscope-camera system installed within the portable incubator system.

2 Claims, 1 Drawing Sheet

(51) Int. Cl.
  *C12M 1/36*   (2006.01)
  *C12M 3/00*   (2006.01)
  *G01N 21/15*  (2006.01)
  *G01N 21/64*  (2006.01)
  *G01N 37/00*  (2006.01)
  *G02B 21/02*  (2006.01)

(52) U.S. Cl.
  CPC ............. *C12M 41/48* (2013.01); *G01N 21/15* (2013.01); *G01N 21/6456* (2013.01); *G02B 21/02* (2013.01); *G01N 2201/0221* (2013.01)

(58) Field of Classification Search
  CPC ............... G01N 21/0332; G01N 21/15; G01N 21/6456; G01N 2201/0221; G01N 2201/0627; G02B 21/06; G02B 21/34
  See application file for complete search history.

(56) References Cited

OTHER PUBLICATIONS

Dhanesh Kattipparambil Rajan, et al., A portable live-cell imaging system with an invert-upright-convertible architecture and a mini-bioreactor for long-term simultaneous cell imaging, chemical sensing and electrophysiological recording, IEEE Access, 2018, pp. 11063-11075, 6.

Kaiqi Su, et al., Smartphone-based portable biosensing system using cell viability biosensor for okadaic acid detection, Sensors and Actuators B: Chemical, 2017, pp. 134-143, 251.

Ke Yang, et al., Mkit: A cell migration assay based on microfluidic device and smartphone, Biosensors and Bioelectronics, 2018, pp. 259-267, vol. 99.

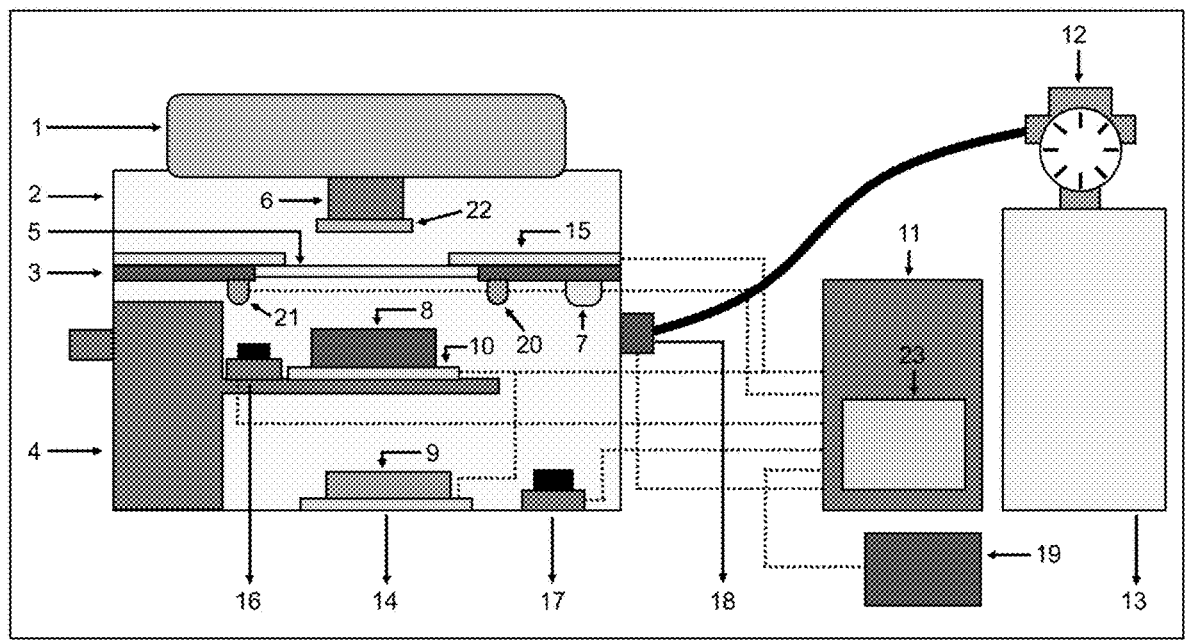

PORTABLE INCUBATOR PLATFORM INTEGRATED INTO A PORTABLE IMAGING DEVICE

CROSS REFERENCE TO THE RELAYED APPLICATIONS

This application is the national stage entry of International Application No. PCT/TR2020/050786, filed on Aug. 31, 2020, which is based upon and claims priority to Turkish Patent Application No. 2019/13661 filed on Sep. 10, 2019, the entire contents of which are incorporated herein by reference.

TECHNICAL FIELD

The invention relates to a portable incubator platform that provides real-time monitoring and data flow of cells integrated into the mobile phone.

BACKGROUND

Incubators are devices used to maintain or reproduce microbiological or cell cultures. Incubators maintain conditions such as optimum temperature, humidity, and carbon dioxide ($CO_2$) content of the atmosphere inside. These devices are frequently used in experimental studies in variety of fields, such as cell biology, microbiology and molecular biology. Incubators are used to culture both bacterial and eukaryotic cells. The phenomena investigated in many cell-based studies are carried out by monitoring the changes in the morphology of the cells. In these studies, cells must be removed from the incubator and examined with an imaging device, e.g., a microscope. However, locating cells in an environment which is not appropriate for their proliferation could have a negative effect and weaken the reliability of the results of the tests based on their behavior. Currently in order to address this problem, there are commercial microscopes that can capture real-time images inside incubators. There are also commercial incubation systems that can be integrated to microscopes. However these technologies rely on expensive, sophisticated and bulky devices.

In that sense, reducing the cost of these systems and making them portable, e.g., small in size and not necessitating advanced infrastructure, could enable the widespread use of cell-based studies on variety of applications, and allow the practicability of cell based treatment methods requiring special infrastructure in the conditions outside of central laboratories.

In recent years, various studies have been carried out on the development of low-cost systems that can capture real-time images without suffering from the cell viability. For example, Walzik et al. (2015) developed a portable and real-time live cell-imaging platform for biomedical research. In this system, sample imaging was realized with a motorized stage and a lens system integrated to a camera. The images taken by the camera were tracked by a computer while different locations within the sample were displayed with the use of the motorized stage. Even though this system is portable, the cost of the system parts (e.g., a custom-made microscopy setup, camera system, and computer) is quite high. A low-cost incubator system similar to this platform was developed by Rajan et al. (2018). In this study, a custom-made microscope setup was developed, and the real-time imaging was achieved by providing an environment suitable for cell proliferation via a small incubator chamber. The system's imaging capability relies on a sophisticated camera based optical setup and computer, which negatively affects portability and cost.

The cost of the optical imaging based on a heavy optical setup, a camera and a computer can be reduced by replacing it with a mobile phone. For example, Su et al. (2017) developed a mobile phone-based portable biosensor system that can monitor cell viability for okadaic acid detection. In another study, Yang et al. (2018) developed a cell migration assay with a microfluidic system integrated to a mobile phone. These systems monitored the vitality of the cells using mobile phone cameras and were able to track their changes over time. With these features brought by these studies, the need for sophisticated optics for sample imaging and a computer for data processing were eliminated. However, in the state of the art, there is no portable and low-cost cell tracking incubation system composed of e.g., a mobile phone and a lens integrated to a small-volume incubator.

SUMMARY

Using a mobile phone, the invention provides real-time tracking of cells and data flow without the need for an expensive, sophisticated and bulky computer-aided lens-camera system, which greatly reduces the cost, provided portability thanks to its small volume and low weight.

With the incubator platform integrated to the mobile phone, cells could proliferate in a healthy way, and reliable data can be produced without being affected by the changes due to the external environment. In addition, the small volume of the incubator system ensures that the environment required for the cells can be effectively controlled and distributed homogeneously inside the incubator.

BRIEF DESCRIPTION OF THE DRAWINGS

The FIGURES prepared to better understand invention, e.g., the portable incubator integrated to a mobile phone are explained below:

FIGURE: The parts of the incubator platform integrated to a mobile phone are shown.

DEFINITIONS OF THE PARTS THAT CONSTITUTE THE INVENTION

1: Mobile Phone
2: Incubation Case
3: Glass Holder
4: Positioning Stage in XYZ-Directions
5: Protective Glass
6: Optical Focusing Apparatus
7: White LED Light Source
8: Sample Container
9: Water Container
10: Heat Pad under Sample Container
11: Micro-Controller
12: Regulator
13: $CO_2$ Tank
14: Heat Pad Under Water Container
15: Heat Pad Around the Protective Glass
16: Temperature-Humidity Sensor
17: $CO_2$ Sensor
18: Safety Valve with a Filter
19: Power Supply
20: Green LED Light Source
21: Red LED Light Source
22: Emission Filter
23: Monitor

DETAILED DESCRIPTION OF THE EMBODIMENTS

A portable incubator platform integrated into a mobile phone (1) that provides real-time tracking of samples and data flow comprises;

An optical focusing apparatus (6), which is positioned in front of a mobile phone lens, and enables high resolution images to be taken, A positioning stage in XYZ directions (4) that enables controlling distance between a sample container (8) and the optical focusing apparatus (6) for displaying the desired points of the sample and achieving high-resolution images, A glass holder (3) preventing fogging due to humidity in incubation case (2) on the mobile phone (1) and the optical focusing apparatus (6), A protective glass (5) placed in the glass holder (3) that allows sample to be monitored by the mobile phone (1)—the optical focusing apparatus (6), A heat pad (15) that prevents the protective glass (5) from fogging, which is positioned on the protective glass (5), At least one white LED light source (7) that helps finding the location of cells in the dark environment of incubator, A heat pad (10) positioned below sample container (8) that provides required temperature for sample inside the incubator, A temperature-humidity sensor (16) that allows temperature and humidity control inside the incubator, A $CO_2$ sensor (17) that enables control of the $CO_2$ ratio inside the incubator, A micro-controller (11) that enables control of LED light sources (7, 20, 21), heat pads (10, 14, 15), temperature-humidity (16) and $CO_2$ sensors (17) and the safety valve (18), At least one power supply (19) that feeds micro-controller (11), A monitor (23) integrated to the micro-controller (11) that allows real-time display of the temperature, humidity and $CO_2$ ratio inside the incubator, At least one $CO_2$ tank (13) that supplies the $CO_2$ required for sample, At least one regulator (12) to maintain the incubator internal atmospheric pressure at a certain level, A safety valve (18) that provides or stops $CO_2$ flow when necessary, A water container (9) containing water that provides necessary humidity for the sample inside the incubator, and heat pad (14) under the water container (9) for evaporation of the water, At least one color LED light source, and a multi-band light emission filter (22) for one-color (or multi-color) fluorescent imaging.

In the incubator platform, which enables real-time tracking of cells and data flow (FIGURE), a mobile phone (1) enables real-time monitoring of the samples (e.g., mammalian cell, bacteria, etc.) in the sample container (8). In order to take reliable and high-resolution images, an optical focusing apparatus (6) with high magnification and low cost, which is developed for mobile phones is placed in front of the lens of the mobile phone. (e.g., magnifier, lens system, etc.). The positioning stage in XYZ directions (4) is used to control the distance between the sample container (8) and the optical focusing apparatus (6) to display the desired locations in focus within the sample.

This optical-imaging section is separated from the incubator with the part denoted as glass holder (3), which prevents possible fogging in the optic lenses due to the humidity inside the incubation case (2) and the effects of the humidity on the electronics of the mobile phone (1). In the glass holder (3), the protective glass (5) is aligned with the optical focusing apparatus (6) and the sample is displayed by the mobile phone—lens system. To further eliminate the fogging of the protective glass (5), it is heated with a heat pad (15) around it.

A white LED (light emitting diode) light source (7) is used to find the location of the cells inside the dark incubator, formed by the incubation case (2) produced with an opaque material.

LED light sources (7, 20, 21), heat pads (10, 14, 15), temperature-humidity (16) and $CO_2$ sensors (17) and safety valve (18) are controlled by a micro-controller (11). The micro-controller (11) is fed by a power supply (19).

Using a monitor (23) integrated to the micro-controller (11), temperature, humidity and $CO_2$ ratio of the incubation environment are shown to the user in real-time.

A feedback mechanism has been created with the temperature-humidity (16) and $CO_2$ sensors (17) controlled by a micro-controller (11) to ensure the continuity of the appropriate temperature, humidity and $CO_2$ amount required for the cells of interest.

Temperature: The temperature required for the cells (e.g., 37° C.) inside the incubator is provided by a heat pad (10) to be placed under the sample container (e.g., a cell flask or a petri dish) (8). The temperature-humidity sensor (16) is used to keep the temperature of the incubator in the desired level by the heat emitted by the heat pad. The temperature-humidity sensor (16) is positioned very close to the sample container (8) such that the temperature of the sample is continuously monitored. If the temperate level is lower/higher than the desired level, the heat pad (10) is started/stopped by the microcontroller (11).

Humidity: The humidity required for the cells is provided by the evaporation of the de-ionized water in the water container (e.g., petri dish) (9) placed on the heat pad (14). The temperature-humidity sensor (16) is used to control the humidity of the incubator and the sensor (16) is controlled by the micro-controller (11). When the humidity level in the incubator falls below the desired level (decrease in the humidity indicates the loss of water in the water container), the user is given a warning and the water container (9) is refilled by the user.

$CO_2$: The $CO_2$ required for the cells is provided by a $CO_2$ tank (13). A regulator (12) is used to maintain the internal atmospheric pressure of the incubatorat a certain level (e.g., 15 psi). The $CO_2$ ratio (e.g., 5%) required for the cells is obtained by mixing 100% $CO_2$ taken from the tank (13) and the air evaporated from the water container (9). The $CO_2$ ratio of the incubator is monitored by a $CO_2$ sensor (17). If the $CO_2$ ratio is lower/higher than the desired level, the $CO_2$ flow is allowed/cut off by starting/stopping the safety valve (18) which is controlled by the micro-controller (11). By attaching a filter to the safety valve (18), dusty particles are prevented from entering the incubator.

In addition, the required areas are covered with sealing pieces (e.g., made of rubber), preventing air intakes that can disturb the balance of the internal environment of the incubator during the moment of movement of mechanical/optical parts.

In the invention, the proliferation of cells can be observed in real-time as in conventional incubator systems.

In addition, one green (20) and one red (21) LED light sources and a multi-band emission filter (22) are added to produce two images required for multi-color fluorescent imaging. In the fluorescence microscope mode of the platform, cellular activities is observed in addition to the proliferation of the cells. Green and red fluorescence imaging is obtained by operating green (20) and red (21) LEDs sequentially, where two different fluorescent images are created for each light source, while using two different emission bands of the emission filter (22). The white LED (7) is used to find the location to be examined on the sample, which is then turned off by the button on the micro-controller (11) during the fluorescence measurement. The user can capture images for only one color (green or red) separately for two colors.

For two images: By using the micro-controller (11), the user can turn on the green (20) and red (21) LED light sources one by one and take two images with one light source at a time. Images are taken with the camera's default (default) focus, white balance, ISO (International Organization of Standardization), integration time and frame rate settings. Multi-color fluorescence images are obtained by combining these captured images with any commercial code or a simple image combination code to achieve a final two-color fluorescence signal.

REFERENCES

Walzik, M. P., Vollmar, V., Lachnit, T., Dietz, H., Haug, S., Bachmann, H., Fath, M., Aschenbrenner, D., Mofrad, S. A., Friedrich, O., Gilbert, D. F. 2015. "A portable low-cost long-term live cell imaging platform for biomedical research and education", Biosensors and Bioelectronics, 64, 639-649.

Rajan, D. K., Kreutzer, J., Valimaki, H., Pekkanen-Mattila, M., Ahola, A., Skogberg, A., Aalto-Setala, K., Ihalainen, H., Kallio, P., Lekkala, J. 2018. "A portable live-cell imaging system with an invert-upright-convertible architecture and a mini-bioreactor for long-term simultaneous cell imaging, chemical sensing and electrophysiological recording", IEEE Access, 6, 11063-11075.

Su, K., Pan, Y., Wan, Z., Zhong, L., Fang, J., Zou, Q., Li, H., Wang, P. 2017. "Smartphone-based portable biosensing system using cell viability biosensor for okadaic acid detection", Sensors and Actuators B: Chemical, 251, 134-143.

Yang, K., Wub, J., Peretz-Sorokab, H., Zhua, L., Lia, Z., Sanga, Y., Hipolitob, J., Zhangc, M., Santosd, S., Hillierc, C., de Fariac, R. L., Liva, Y., Linb, F. 2018. "Mkit: A cell migration assay based on microfluidic device and smartphone", Biosensors and Bioelectronics, 99, 259-267.

What is claimed is:

1. A portable incubator platform integrated into a mobile phone providing a real-time tracking of samples and data flow, comprising;

an optical focusing apparatus, wherein the optical focusing apparatus is positioned in a front of a mobile phone lens, and the optical focusing apparatus enables high resolution images to be taken, a positioning stage in XYZ directions, wherein the positioning stage in XYZ directions enables controlling a distance between a sample container and the optical focusing apparatus for displaying desired points of a sample and achieving the high-resolution images, a glass holder preventing fogging due to humidity in an incubation case on the mobile phone and the optical focusing apparatus, a protective glass placed in the glass holder allowing the sample to be monitored by the mobile phone a first heat pad preventing the protective glass from fogging, wherein the first heat pad is positioned on the protective glass, at least one white LED light source, wherein the at least one white LED light source helps finding a location of cells, a second heat pad positioned below the sample container, wherein the second heat pad provides a required temperature for the sample, a temperature-humidity sensor allowing a temperature and humidity control, a $CO_2$ sensor enabling a control of a $CO_2$ ratio, a micro-controller enabling a control of the at least one white LED light source, at least one red LED light source, at least one green LED light source, the first heat pad, the second heat pad, a third heat pad, the temperature-humidity sensor and the $CO_2$ sensor, and a safety valve, at least one power supply feeding a micro-controller, a monitor integrated to the micro-controller, wherein the monitor allows a real-time display of a temperature, a humidity and the $CO_2$ ratio, at least one $CO_2$ tank supplying $CO_2$ required for the sample, at least one regulator configured to maintain an incubator internal atmospheric pressure at a certain level, the safety valve providing or stopping a $CO_2$ flow when necessary, a water container containing water, wherein the water container provides a necessary humidity for the sample and the third heat pad under the water container for evaporation of the water, and at least one color LED light source, and a multi-band light emission filter for one-color or multi-color fluorescent imaging.

2. The portable incubator platform according to claim 1, further comprising the at least one green LED light source, the at least one red LED light source, and the multi-band light emission filter enabling a fluorescence imaging of cellular activities.

* * * * *